United States Patent [19]

Hofmann

[11] Patent Number: 4,482,503

[45] Date of Patent: Nov. 13, 1984

[54] PROCESS FOR PRODUCING ALIPHATIC NITRILES

[75] Inventor: Peter Hofmann, Marl, Fed. Rep. of Germany

[73] Assignee: Chemische Werke Huels AG, Marl, Fed. Rep. of Germany

[21] Appl. No.: 400,026

[22] Filed: Jul. 20, 1982

[30] Foreign Application Priority Data

Aug. 13, 1981 [DE] Fed. Rep. of Germany ....... 3131968

[51] Int. Cl.³ .................. C07C 120/00; C07C 120/08
[52] U.S. Cl. ................................................. 260/465.2
[58] Field of Search ...................................... 260/465.2

[56] References Cited

U.S. PATENT DOCUMENTS

| | | | |
|---|---|---|---|
| 2,205,076 | 6/1940 | Wortz | 260/465.2 |
| 2,334,192 | 11/1943 | Hanford | 260/465.2 |
| 2,369,061 | 2/1945 | Loder et al. | 260/465.2 |
| 2,439,426 | 4/1948 | Gresham | 260/465.2 |
| 2,808,426 | 10/1957 | Potts et al. | 260/465.2 |
| 2,955,130 | 10/1960 | Guyer et al. | 260/465.2 |
| 3,299,117 | 1/1967 | Potts | 260/465.2 |
| 3,538,018 | 11/1970 | Pilch et al. | 260/465.2 |
| 3,836,567 | 9/1974 | Krekeler et al. | 260/465.2 X |
| 4,234,509 | 11/1980 | Billenstein et al. | 260/465.2 |

FOREIGN PATENT DOCUMENTS

| | | | |
|---|---|---|---|
| 508190 | 12/1954 | Canada | 260/465.2 |
| 773140 | 12/1967 | Canada | 260/465.2 |

OTHER PUBLICATIONS

Mitchell et al., J.A.C.S., (53), 1931, pp. 321–330.

Primary Examiner—Joseph Paul Brust

[57] ABSTRACT

A process for producing aliphatic nitriles by reacting the corresponding carboxylic acids or carboxylic alkylesters with ammonia in the liquid phase and in the presence of a metal-containing catalyst, the reaction being carried out at a temperature between about 150° and 290° C. in the presence of iron or an iron compound as the catalyst.

6 Claims, 1 Drawing Figure

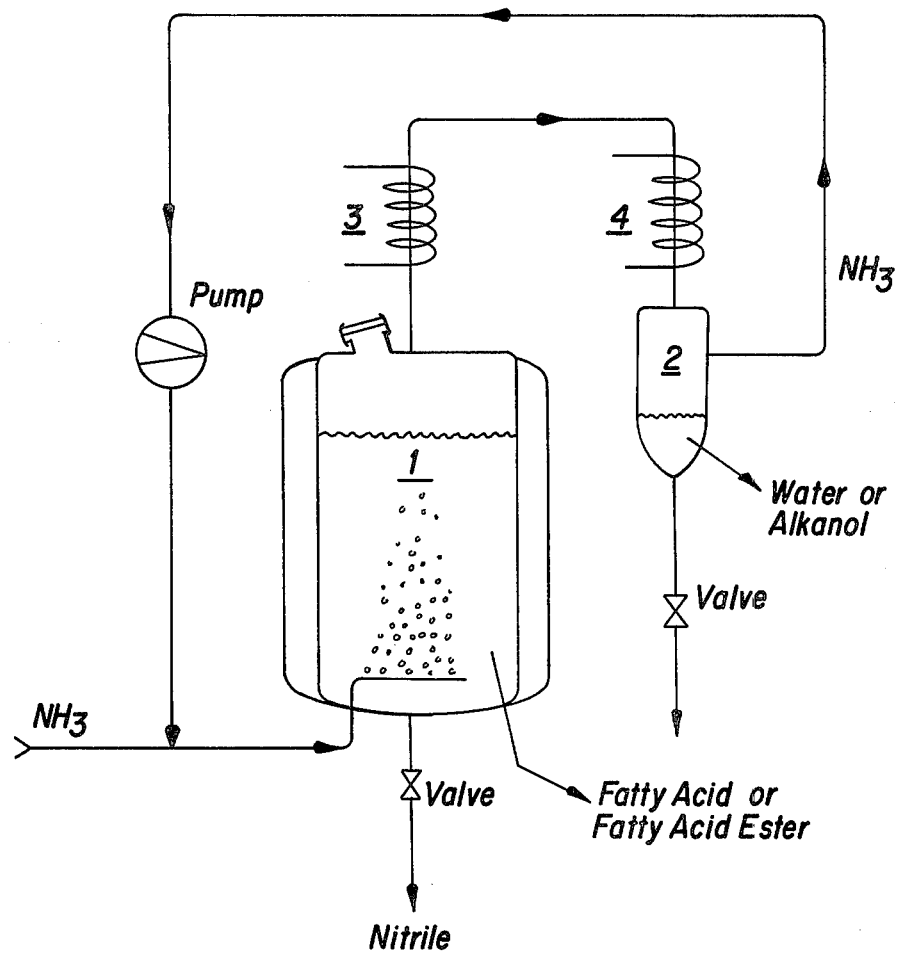

PROCESS FOR PRODUCING ALIPHATIC NITRILES

CROSS-REFERENCE TO RELATED APPLICATIONS

The disclosure of inventor Hofmann's copending application, Ser. No. 125,482, filed Feb. 28, 1980, and now abandoned, and U.S. Pat. Nos. 3,883,587 and 3,935,228 cited therein are incorporated herein to show alkoxycarbonylation procedures carried out in the presence of cobalt catalysts and a promoter from the group pyridine, nonortho-substituted alkylpyridine and mixtures thereof.

BACKGROUND OF THE INVENTION

The field of the invention is the production of nitriles and the present invention is particularly concerned with the liquid phase reaction of carboxylic acids or carboxylic alkylesters with ammonia in the presence of an iron catalyst.

The state of the art of nitrile production may be ascertained by reference to the Kirk-Othmer, "Encyclopedia of Chemical Technology", 2nd edition, Supplemental Volume (1971), pp. 590–603 under the section NITRILES, particularly pp. 592–593 and U.S. Pat. Nos. 1,991,955; 2,061,314; 2,177,619; 2,205,076; 2,493,637; 2,546,521; 2,555,606; 2,794,043; 2,808,426 and 2,993,926, the disclosures of which are incorporated herein.

Aliphatic nitriles are produced commercially and almost exclusively by reacting fatty acids or derivatives of these fatty acids with ammonia. In the gas phase production, the process is carried out with the vapors of the fatty acids or their derivatives, especially esters, passing together with ammonia at temperatures between 320° and 600° C. over dehydrating catalysts. The applicable catalysts include aluminum oxide, silica gel, oxides of thorium, titanium, molybdenum, tungsten and vanadium as disclosed in U.S. Pat. Nos. 1,991,955; 2,177,619; and 2,205,076; the article of J. A. Mitchell, E. E. Reid, published in the J. Amer. Chem. Soc. 53, 321 (1931) and the article in J. Appl. Chem USSR 45, 1824 (1972).

The high thermal loading on the input materials and the reaction products, and also as regards the apparatus required to carry out the reaction, can be reduced by operating in the liquid phase. However the liquid phase reaction still requires temperatures up to 350° C. and requires a high pressure of reaction for low boiling point input materials as disclosed in U.S. Pat. Nos. 2,061,314; 2,546,521; and 2,555,606; and the article by R. L. Kenyon, D. V. Stingley, and H. P. Young, in Ind. Eng. Chem. 42, 202 (1950).

It is possible to further lower the temperature of reaction when operating in the liquid phase by using special catalysts. No reaction temperatures exceeding 315° C. are required in the presence of the alcohol esters of titanium, zirconium or hafnium as disclosed in U.S. Pat. No. 2,993,926. When cobalt salt is used as the catalyst, the maximum temperature can be restricted to 290° C. as disclosed in U.S. Pat. No. 2,493,637. The last two cited methods however suffer from the limitation of requiring the use of relatively costly catalysts which are reusable only to a limited degree.

SUMMARY OF THE INVENTION

Having in mind the limitations of the prior art it is an object of the present invention to provide a process for producing aliphatic nitriles by reacting the corresponding carboxylic acids or carboxylic alkylesters in the liquid phase with ammonia by maintaining temperatures generally below those of the prior art and further allowing the use of economical catalysts which do not affect the process economy.

This object is accomplished by reacting carboxylic acids or carboxylic alkylesters having 4 to 22 carbon atoms with ammonia in the liquid phase at a temperature of about 150° to 290° C. and in the presence of an iron containing catalyst to produce the aliphatic nitriles corresponding to the carboxylic acids and alkylesters.

BRIEF DESCRIPTION OF THE DRAWING

The FIGURE of the accompanying drawing is a schematic representation of one type of apparatus which may be used in carrying out the improved methods of the present invention.

Reaction vessel 1 has a heating jacket and the vessel is discontinuously loaded and emptied. Water or alkanol is separated from separator 2. The temperature of condenser 3 is greater than that of condenser 4. The temperature of the condensers is set so that all ingredients of the reaction mixture, except for water, alkanol, and $NH_3$, are condensed in condenser 3.

DESCRIPTION OF THE PREFERRED EMBODIMENTS

The results of the present invention are new and unexpected because according to the statements in U.S. Pat. No. 2,205,076 on page 3, left column, lines 17 through 19, it was not to be expected that iron and iron compounds exert a positive catalytic action. According to the disclosures made in U.S. Pat. No. 2,205,076, iron favors undesired side reactions such as the cracking of the products. For that reason the patent proposes the use of apparatus made of aluminum and preferably nickel.

It is further surprising that the catalyst of the present invention allows reacting fatty acids and fatty acid esters with nearly the same results. The few examples known from the literature dealing with the production of nitriles based on fatty acid esters and disclosing data about it show that using esters always involves serious drawbacks particularly the article of J. A. Mitchell and E. E. Reid in the J. Amer. Chem. Soc. 53, 321 (1931). According to this article the lives of the catalysts used in the gas-phase production of nitriles drop sharply when esters are used as compared to the use of free acids. Contrary to the fatty-acid based high yields ordinarily obtained from the liquid phase methods from producing nitriles, only yields of 60 to 65% are obtained when methylesters are the raw products as disclosed by P. B. Jonardhan, J. Sci. Ind. Research India 9B, 208, (1950).

The reaction of fatty acid esters in the presence of alcohol esters of titanium, zirconium or hafnium by the method disclosed in U.S. Pat. No. 2,993,926 can result in the formation of volatile alcohol esters of titanium, zirconium or hafnium especially when esters of lower alcohols, for instance methanol or ethanol are present, because of the re-esterification with the catalyst and these volatile alcohol esters can easily be discharged with ammonia from the reactor.

Again this process step is far from being unrestrictedly applicable, at least as regards the use of fatty acid esters.

Suitable carboxylic acids for the process of the present invention on the one hand, and preferredly, are straight-chain and branched saturated aliphatic monocarboxylic acids having 4 to 22 C atoms, and on the other hand also unsaturated aliphatic monocarboxylic acids and aliphatic dicarboxylic acids having 4 to 22 C atoms. Furthermore, the alkylesters of these carboxylic acids having 1 to 8, preferably 1 to 4 C atoms in the alkanol group can be used.

Typical representative substances are the acids: butyric, valeric, capronic, enanthic, caprylic, pelargonic, capric, lauric, myristic, palmitic, stearic, archic, behenic, oleic, suberic and dodecane di-acid, as well as the esters of these acids with monoalkanols such as methanol, ethanol, n-propanol, iso-propanol, n-butanol, iso-butanol and pentanol.

The carboxylic acids and carboxylic-acid alkylesters suitable for the process of the present invention can be prepared for instance by saponifying or re-esterifying natural raw materials (oil and fats). However, carboxylic acids or carboxylic alkylesters prepared on the basis of petrochemical synthetic methods are equally suitable. Applicable among these are for instance the procedures of alkoxycarbonylation or hydrocarboxy-alkylation of olefins as disclosed in U.S. patent application Ser. No. 125,482, the hydroformylation of olefins with ensuing oxidation of the primary reaction products into carboxylic acids as disclosed by J. Falbe, New synthesises with Carbon Monoxide, Springer publishers, Berlin, Heidelberg, New York (1980) and the oxidation of paraffins as disclosed by H. Weissermel, H. J. Arpe, Industrielle Organische Chemie, 2nd ed., p. 196, Chemie publishers, Weinheim, New York (1978).

Iron as well as iron compounds have been found suitable as catalysts for the process of the present invention. Suitable iron compounds for instance are salts of iron with inorganic or organic acids such as chlorides, nitrates, sulfates, acetates, naphthenates, laurates, palmitates, stearates or oxides of iron such as $Fe_2O_3$. The valence of the iron in the iron compounds is immaterial, that is, compounds both of divalent and of trivalent iron can be used. It is advantageous when using iron that it be in a most finely distributed form such as chips or powders.

The amount of the catalyst used in the form of an iron compound or as metallic iron as a rule will be from 0.01 to 5, preferably 0.3 to 3% by weight of iron referred to the carboxylic acid or the carboxylic alkylester.

The reaction of the carboxylic acids or carboxlic alkylesters with ammonia in the presence of the catalyst is carried out in the process of the present invention at a temperature between about 150° and 290° C., preferably between 180° and 265° C. This means that the process of the present invention can be carried out in principle at zero gauge pressure when carboxylic acids or carboxylic alkylesters having a boiling point which at standard pressure exceeds 150° C. are used. A particularly simple procedure permitting doing without pressure-resistant equipment is available whenever the boiling point of the particular substrate (carboxylic acid or carboxylic alkylester) exceeds 150° C. and the temperature of reaction does not exceed the boiling point.

A conventional implementation of the process of the invention consists in placing the substrate together with the catalyst dissolved or suspended therein in an agitation vessel as shown in the drawing and by introducing ammonia with heating until complete reaction has taken place. The unused ammonia following the condensation of the water or the water/alkanol mixture discharged concurrently can be fed back into the reaction. Besides this discontinuous operation other modes of implementation obviously are possible that allow a continuous implementation.

The nitriles prepared by the process of the present invention can be used for instance as solvents, softening agents, synthetic fibers and textile auxiliary means. The amines which are easily obtained from the nitriles by hydrogenation are applicable for instance as raw materials in the production of cationic surfactants, emulsifiers and corrosion inhibitors.

Specific examples of the nitriles prepared according to the present invention are nitriles of butyric, valeric, capronic, enanthic, caprylic, pelargonic, capric, lauric, myristic, palmitic, stearic, archic, behenic, oleic, suberic acid and dodecane di-acid, as well as mixtures of nitriles of acids having 4 to 22 carbon atoms, which can be prepared by hydrocarboxylation or hydrocarboxyalkylation of olefins having 3 to 21 carbon atoms.

The examples below more closely explain the process of the present invention.

EXAMPLES 1 THROUGH 8

A mixture of isomeric dodecanoic-acid methylesters (53% molar) with an n-proportion of 77% by weight and tridecanoic-acid methylesters (47% molar) with an n-proportion of 75% by weight was used to produce nitriles, this mixture itself having been prepared by alkoxycarbonylating a mixture of isomeric n-undecenes and n-dodecenes (with an alpha proportion less than 1% by weight in each case) by the method of U.S. patent application No. 125,482. The alkoxycarbonylation reaction was carried out while observing the following quantitative proportions, 0.5 moles of n-undecene
0.5 moles of n-dodecene
2 moles of methanol
0.4 moles of gamma-picoline
0.04 gram-atoms of cobalt in the form of a cobalt-naphthenate containing 10% by weight of cobalt in a 50-liter autoclave and under the following conditions of reaction,

| | |
|---|---|
| Temperature of reaction | 185° C. |
| Carbon monoxide pressure | 180 bars |
| (CO contains 1.5% by volume of $H_2$) | |
| Time of reaction | 55 minutes. |

The reaction mixture obtained under these conditions was used to prepare by distillation the ester mixture of examples 1 through 8. The reaction was carried out with the catalysts listed in table 1 and in such amounts that 1% by weight of metal was present referred to the ester mixture. One tenth of the stoichiometric amount of $NH_3$ was introduced per hour at a temperature of reaction of 250° C. The progress of the reaction could be monitored from the amount of the mixture of alcohol/water discharged together with unconverted $NH_3$ and then being condensed and moreover by the gas-chromatographic analysis of the reaction mixture. The nitrile product of Examples 1–8 is a mixture of nitriles of isomeric $C_{12}$- and $C_{13}$-carboxylic acids.

TABLE 1

| Example # | 1 | 2 | 3 | 4 |
|---|---|---|---|---|
| catalyst | iron | Fe—III | iron | Fe—III |

TABLE 1-continued

|  | powder | nitrate | oxide (Fe$_2$O$_3$) | chloride |
|---|---|---|---|---|
| Reaction time for complete conversion (h) | 15 | 14 | 14 | 13 |

| Example # | 5 | 6 | 7 | 8 |
|---|---|---|---|---|
| catalyst | Fe—II sulfate | Fe—III sulfate | Fe—laurate[1] | Fe—naphthenate[1] |
| Reaction time for complete conversion (h) | 13 | 13 | 12 | 12 |

[1]iron content: 10% by weight

EXAMPLES 9 THROUGH 16

The substrates listed in table 2 were converted into nitriles under the conditions for example 8.

TABLE 2

| Example # | 9 | 10 | 11 | 12 | 13 | 14 | 15 | 16 |
|---|---|---|---|---|---|---|---|---|
| Substrate | Lauric acid methyl-ester | Stearic acid methyl-ester | Lauric acid ethyl-ester | Lauric acid butyl-ester | Pelargonic acid | Mixture of 50% molar of dodecanoic acid (n-proportion 77% by wt) and 50% molar of tridecanoic acid (n-proportion 75% by wt) | Oleic acid | Dodecane-diacid |
| Reaction time for complete conversion (h) | 12 | 14 | 12 | 14 | 12 | 12 | 14 | 13 |
| Nitrile Products | Lauric acid nitrile | Stearic acid nitrile | Lauric acid nitrile | Lauric acid nitrile | Pelargonic acid nitrile | Mixture of nitriles of isomeric C$_{12}$— and C$_{13}$ carboxylic acids | Oleic acid nitrile | Dodecane-diaciddi-nitrile |

EXAMPLES 17 THROUGH 19

Example 9 was repeated at different temperatures of reaction.

TABLE 3

| Example # | 17 | 18 | 19 |
|---|---|---|---|
| Temperature of reaction (°C.) | 200 | 230 | 260 |
| Reaction time for complete conversion (h) | 20 | 15 | 12 |

EXAMPLES 20 AND 21

Example 9 was repeated for various catalyst concentrations (pure metal in % by weight referred to the substrate).

TABLE 4

| Example # | 20 | 21 |
|---|---|---|
| Catalyst concentration (% by weight) | 0.5 | 2 |
| Reaction time for complete conversion (h) | 16 | 14 |

EXAMPLE 22

Example 9 was repeated except that 1/6 of the stoichiometric amount of NH$_3$ was introduced per hour. The time required for complete conversion was 7.5 h.

EXAMPLE 23

The reaction mixture obtained per example 8 was reprocessed by distillation. The residue so obtained and containing all of the iron used as catalyst was reused as the catalyst under the conditions of example 8. Again the time of reaction required for complete conversion was 12 h.

The nitriles obtained in the examples 1 through 23 evinced a purity in excess of 95% by weight after complete conversion.

I claim:

1. A single vessel batch process for producing aliphatic mononitriles comprising:
    (a) mixing a substrate selected from the group consisting of carboxylic acids having 4 to 22 carbon atoms or carboxylic alkylesters of carboxylic acids having 4 to 22 carbon atoms, and monoalkanols having 1 to 8 carbon atoms with a catalyst consisting of iron or compounds selected from the group consisting of iron chlorides, iron nitrates, iron sulfates, iron acetates, iron naphthenates, iron laurates, iron palmitates, iron stearates, and iron oxides in a liquid phase, wherein said catalyst has a concentration of about 0.3 to 3 percent by weight of iron;
    (b) adding excess ammonia to said liquid phase as a reactant;
    (c) heating the reactants of (a) and (b) in said liquid phase at a temperature of about 150° to 290° C. to form mononitriles corresponding to said carboxylic acids or said carboxylic alkylesters; and
    separating said mononitriles by distillation.

2. The process of claim 1, wherein the reaction of step (c) is carried out at a temperature between 180° and 265° C.

3. A single vessel batch process for producing aliphatic mononitriles comprising:
    (a) mixing a substrate selected from the group consisting of carboxylic acids having 4 to 22 carbon atoms or carboxylic alkylesters of carboxylic acids having 4 to 22 carbon atoms, and monoalkanols having 1 to 8 carbon atoms with a catalyst consisting of iron or compounds selected from the group consisting of iron chlorides, iron nitrates, iron sulfates, iron acetates, iron naphthenates, iron laurates, iron palmitates, iron stearates and iron oxides in a liquid phase wherein said catalyst has a concentration of about 0.3 to 3% by weight of iron;
    (b) adding excess ammonia to said liquid phase as a reactant;
    (c) heating the reactants of (a) and (b) in said liquid phase at a temperature of about 180° to 265° C. to form mononitriles corresponding to said carboxylic acids or said carboxylic alkylesters; and
    (d) separating said mononitriles by distillation.

4. The process of claim 3, wherein said catalyst consists of iron in finely distributed form.

5. The process of claim 3, wherein said carboxylic acids and said carboxylic alkylesters have boiling points in excess of temperatures of step (c).

6. The process of claim 3, wherein said mononitriles are selected from the group consisting of butyric acid nitriles, valeric acid nitrile, capronic acid nitrile, enanthic acid nitrile, caprylic acid nitrile, pelargonic acid nitrile, capric acid nitrile, lauric acid nitrile, myristic acid nitrile, palmitic acid nitrile, stearic acid nitrile, archic acid nitrile, behenic acid nitrile, oleic acid nitrile, suberic acid nitrile, and mixtures thereof.

* * * * *